(12) United States Patent
Meriles

(10) Patent No.: US 10,330,750 B2
(45) Date of Patent: Jun. 25, 2019

(54) METHOD AND APPARATUS FOR POLARIZING NUCLEAR AND ELECTRONIC SPINS

(71) Applicant: Research Foundation of The City University of New York, New York, NY (US)

(72) Inventor: Carlos A. Meriles, Fort Lee, NJ (US)

(73) Assignee: Research Foundation of the City University of New York, New York, NY (US)

( * ) Notice: Subject to any disclaimer, the term of this patent is extended or adjusted under 35 U.S.C. 154(b) by 672 days.

(21) Appl. No.: 14/781,127

(22) PCT Filed: Apr. 7, 2014

(86) PCT No.: PCT/US2014/033175
§ 371 (c)(1),
(2) Date: Sep. 29, 2015

(87) PCT Pub. No.: WO2014/165845
PCT Pub. Date: Oct. 9, 2014

(65) Prior Publication Data
US 2016/0054402 A1 Feb. 25, 2016

Related U.S. Application Data

(60) Provisional application No. 61/808,664, filed on Apr. 5, 2013.

(51) Int. Cl.
*G01R 33/30* (2006.01)
*G01R 33/28* (2006.01)
(Continued)

(52) U.S. Cl.
CPC ......... *G01R 33/302* (2013.01); *G01R 33/282* (2013.01); *G01N 24/08* (2013.01);
(Continued)

(58) Field of Classification Search
CPC .... G01R 33/282; G01R 33/302; G01R 33/62; G01R 33/307; G01N 24/08; G01N 24/12
See application file for complete search history.

(56) References Cited

U.S. PATENT DOCUMENTS 6,194,900 B1 * 2/2001 Freeman .............. G01R 33/302
324/318
8,455,278 B2 * 6/2013 Linares .................. B82Y 10/00
216/2

(Continued)

FOREIGN PATENT DOCUMENTS

| WO | WO2012034924 | 3/2012 |
|---|---|---|
| WO | WO2012174019 | 12/2012 |
| WO | 2016188557 | 12/2016 |

OTHER PUBLICATIONS

ISA/US; International Search Report for PCT/US2014/033175; Aug. 20, 2014; US.

(Continued)

*Primary Examiner* — Patrick Assouad
*Assistant Examiner* — Haidong Zhang
(74) *Attorney, Agent, or Firm* — Peter J. Mikesell; Schmeiser, Olsen & Watts, LLP

(57) ABSTRACT

A method and apparatus for polarizing nuclear or electronic spins is disclosed. An analyte is passed near a surface that has a plurality of spin defect centers implanted within 10 nm of the surface. The spin defect centers are exposed to a magnetic field and illumination to produce polarized spins. The polarized spins then induce spin polarization in the analyte.

18 Claims, 10 Drawing Sheets

(51) Int. Cl.
    *G01N 24/08*    (2006.01)
    *G01N 24/12*    (2006.01)
    *G01R 33/62*    (2006.01)

(52) U.S. Cl.
    CPC ............ *G01N 24/12* (2013.01); *G01R 33/307* (2013.01); *G01R 33/62* (2013.01)

(56) References Cited

U.S. PATENT DOCUMENTS

| | | | |
|---|---|---|---|
| 2006/0001423 A1* | 1/2006 | Barbic .................. | G01R 33/20 324/300 |
| 2011/0062957 A1* | 3/2011 | Fu ........................ | G01N 24/088 324/307 |
| 2011/0066108 A1* | 3/2011 | Geipel .................. | A61M 5/141 604/151 |
| 2011/0163291 A1 | 7/2011 | Scarsbrook et al. | |
| 2012/0051996 A1* | 3/2012 | Scarsbrook ............ | B82Y 10/00 423/446 |
| 2014/0035584 A1* | 2/2014 | Twitchen .......... | B01L 3/502707 324/321 |

OTHER PUBLICATIONS

Staudacher, T. et al.; Nuclear Magnetic Resonance Spectroscopy on a (5-Nanometer)3 Sample Volume; Science; Feb. 1, 2013; pp. 561-563; vol. 339, No. 6119.
EPO; Extended European Search Report for EP Application 14778623.0; dated Dec. 22, 2016;.

\* cited by examiner

FIG. 5A FIG. 5B
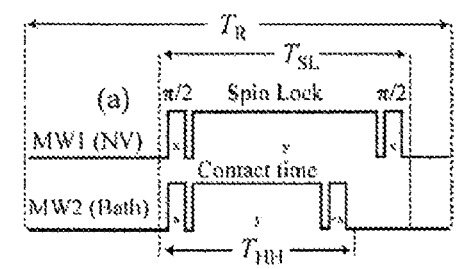 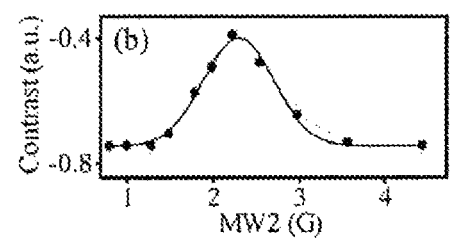
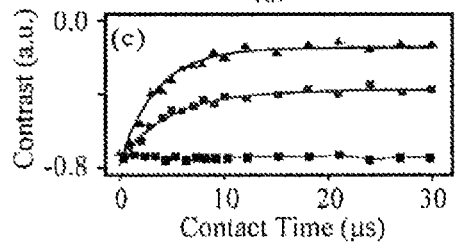 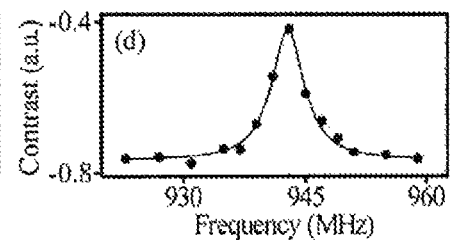
FIG. 5C FIG. 5D

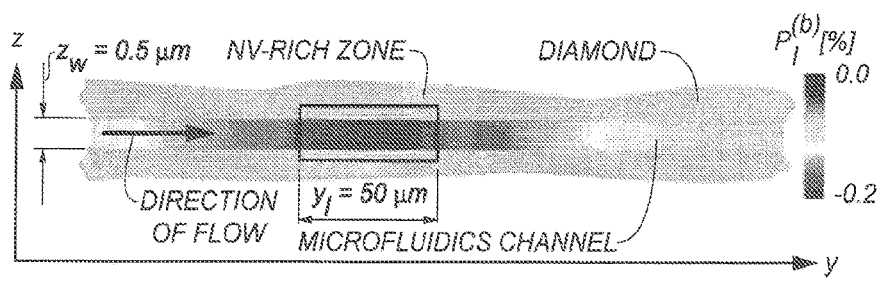
FIG. 7A
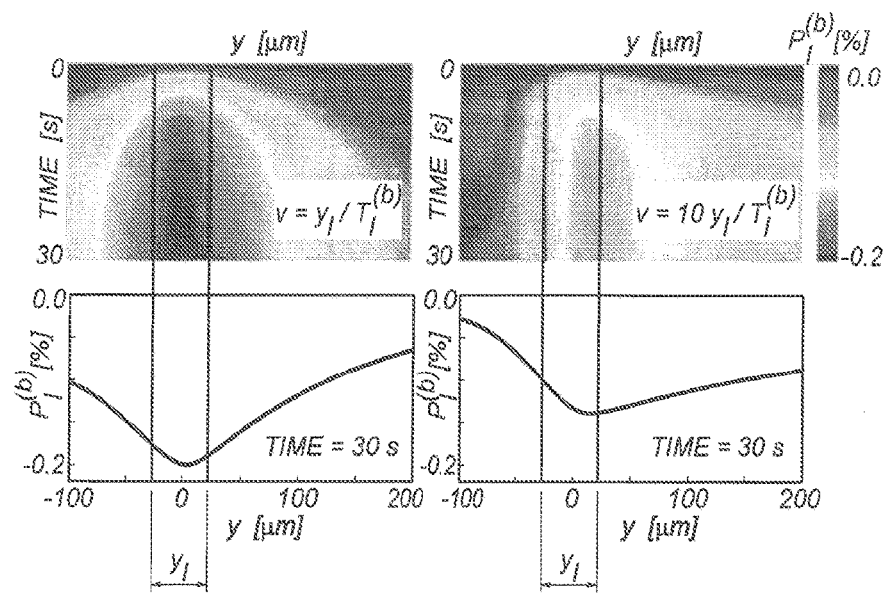
FIG. 7B   FIG. 7C

METHOD AND APPARATUS FOR POLARIZING NUCLEAR AND ELECTRONIC SPINS

STATEMENT OF FEDERALLY SPONSORED RESEARCH OR DEVELOPMENT

This invention was made with government support under contract no. 1111410 and 1309640 awarded by the National Science Foundation (NSF). The government has certain rights in the invention.

CROSS-REFERENCE TO RELATED APPLICATIONS

This application is a non-provisional of U.S. Patent Application Ser. No. 61/808,664 (filed Apr. 5, 2013), the entirety of which is incorporated herein by reference.

BACKGROUND OF THE INVENTION

The subject matter disclosed herein relates to magnetic resonance including nuclear magnetic resonance and electron magnetic resonance.

Magnetic resonance (MR) is one of the most powerful analytical tools employed in the physical, biological, and materials sciences, as well as in medical diagnostics. Nuclei and electrons in a sample under investigation may be thought of as microscopic compasses called spins. In a MR device, a magnet is used to induce spin polarization in the sample (i.e., to partially align these compasses with the external magnetic field). Ultimately, the MR signal in a measurement is proportional to the degree of alignment, which, in turn, increases with the applied field. For this reason, bulky, very-expensive magnets are used whose sole purpose is to produce the highest possible fractional spin alignment and thus the highest signal-to-noise ratio when probing the smallest amount of sample. Unfortunately, and even with the strongest possible magnets, the fractional (nuclear) spin alignment is very low, reaching at room temperature a value of approximately 0.005% or less (i.e., in a hypothetical sample of 1 million nuclear spins, the number difference between spins pointing with the field and against it amounts to less than 50).

Spin polarization is an important parameter to magnetic resonance and thus to analytical science. Some strategies of dynamic polarization of nuclear spins have been introduced in the past. However, they either work at very low temperatures (10 K and below) or are incapable of generating polarization superior to that obtained with the use of a strong magnet. Despite these limitations, higher spin polarization is in such high demand that several companies have developed complex (and very expensive) instruments that partly overcome these problems. Here the sample is cooled down to very low temperatures and subsequently hyperpolarized and quickly transferred to a high-field magnet in the form of a polarized fluid. Such systems are bulky and costly. An alternative method of providing spin polarization is therefore desired.

The discussion above is merely provided for general background information and is not intended to be used as an aid in determining the scope of the claimed subject matter.

BRIEF DESCRIPTION OF THE INVENTION

A method and apparatus for polarizing nuclear or electronic spins is disclosed. An analyte is passed near a surface that has a plurality of spin defect centers implanted within 10 nm of the surface. The spin defect centers are exposed to a magnetic field and illumination to produce polarized spins. The polarized spins then induce spin polarization in the analyte.

In a first embodiment, a method for polarizing nuclear or electronic spins is disclosed. The method comprises steps of introducing an analyte into a channel, wherein at least one surface of the channel is a substrate comprising a plurality of spin defect centers implanted within 10 nm of the at least one surface of the channel. The spin defect centers are exposed to a magnetic field while the analyte is in the channel and illuminated with light to produce polarized spins in the spin defect centers. The polarized spins in the spin defect centers are permitted to induce spin polarization in the analyte.

In a second embodiment, a substrate for polarizing nuclear or electronic spins is disclosed. The substrate comprises a fluid channel wherein at least one surface of the fluid channel comprises a plurality of spin defect centers implanted within 10 nm of the at least one surface. The spin defect center are present in a concentration between about $10^{11}$ and $10^{13}$ spin defect centers per square centimeter within 10 nm of the at least one surface.

In a third embodiment, a substrate for polarizing nuclear or electronic spins is disclosed. The substrate comprises a fluid channel wherein at least one diamond surface of the fluid channel comprises a plurality of nitrogen-vacancy spin defect centers implanted within 10 nm of the at least one diamond surface. The nitrogen-vacancy spin defect centers are present in a concentration between about $10^{11}$ and $10^{13}$ nitrogen-vacancy spin defect centers per square centimeter within 10 nm of the at least one diamond surface.

An advantage that may be realized in the practice of some disclosed embodiments of the disclosed apparatus and method is that a greater degree of spin polarization may be achieved in a sample at room temperature compared to conventional room temperature approaches. This increases the sensitivity of the apparatus and methods.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 2A is a schematic of a polarization system for use with the method of FIG. 1, while

FIG. 5A-D are graphs depicting the results of a Hartman-Hahn protocol;

FIG. 7A, FIG. 7B and FIG. 7C depict polarization changes in a microfluidic channel.

DETAILED DESCRIPTION OF THE INVENTION

The technology disclosed in this specification addresses the fractional spin polarization limitation of magnetic resonance. A sample under investigation is brought in direct contact with the surface of a properly treated diamond crystal exposed to continuous green light. A level of polarization of the order 1-10% can be produced depending on the exact parameters. This level of polarization is up to five orders of magnitude higher than that possible by the application of an external magnetic field under traditional conditions. Because the signal observed in magnetic resonance is proportional to the level of spin polarization attained, the disclosed technology enables the characterization of samples with unprecedented sensitivity. Since only a small magnetic field is required (e.g., produced via permanent ferromagnetic material), the system may be portable. Example applications include the detection of contaminants or pathogens within fluids, the high-throughput characterization of drugs, proteins, or other bio-molecules in solution, the polarization of nanometer thick layers of compound deposited on a surface, etc. As a whole, these capabilities will have a broad impact with applications in laboratory and point-of-care diagnostics, food safety, environmental testing, scientific studies of mass-limited systems, national security, etc.

In one embodiment, the disclosed technology takes advantage of the so-called Nitrogen-Vacancy centers (NV) centers in diamond. The NVs are defects in the diamond crystalline lattice (otherwise formed by carbon atoms) comprising a substitutional nitrogen adjacent to a vacancy (an empty lattice site). The (electronic) spin associated with these centers can be polarized to almost 100% at room temperature simply by illuminating with green light. NV centers can be created very close to the crystal surface via an ion implantation and annealing protocol. One can use these near-surface NVs to sense other spins deposited on the diamond surface. The system comprises a diamond crystal containing implanted NVs, a laser to generate NV polarization, and a microfluidic structure to bring the liquid (or gas) in close contact with the diamond surface. To optimize the transfer, the diamond crystal can be patterned so as to maximize the surface in contact with the fluid.

Figure 1:
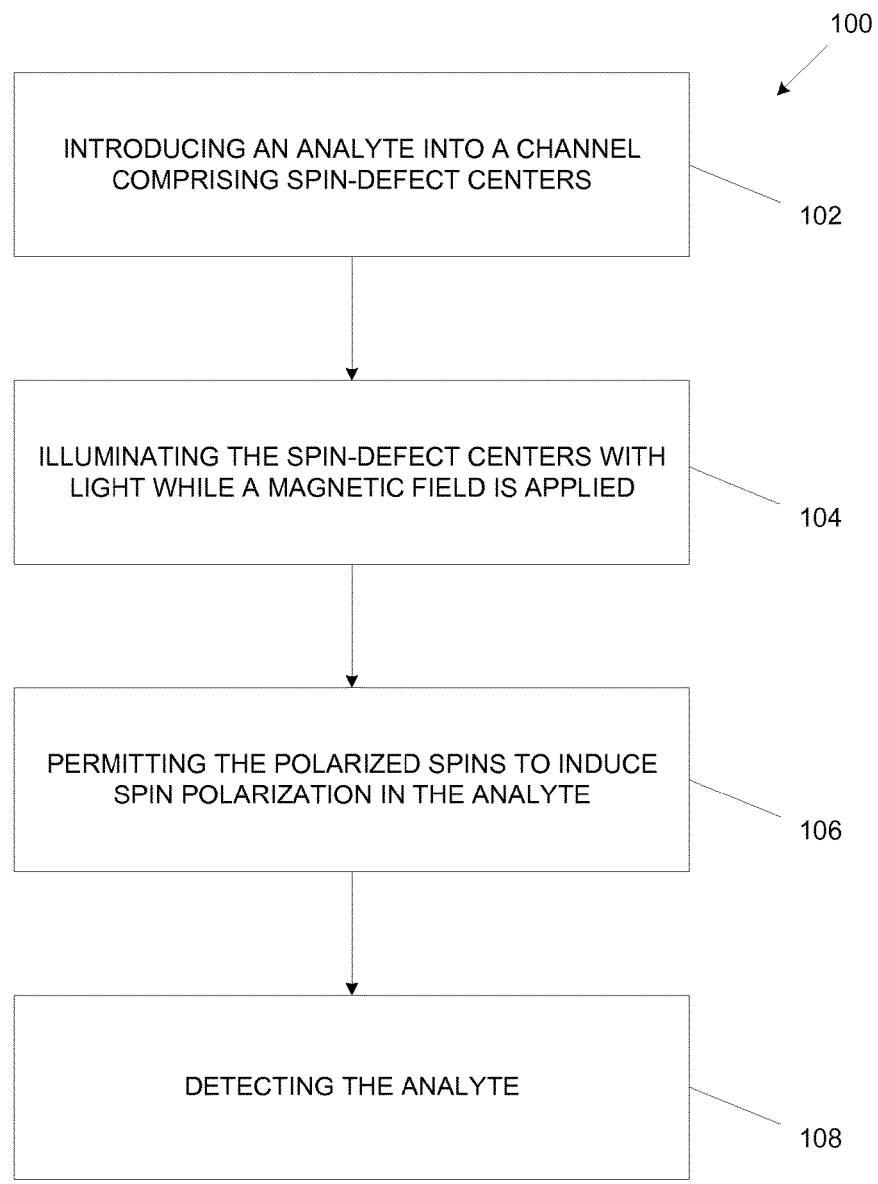
FIG. 1 is a flow diagram of one method for aligning spins.

FIG. 1 is a flow diagram of a method 100 for polarizing nuclear or electronic spins. In step 102, an analyte is introduced into a channel that comprises spin defect centers proximate the surface of a substrate. Examples of substrates include diamond (which have nitrogen-vacancy (NV) defect centers) and silicon carbide (which have PL5 and/or PL6 defect centers). Other examples include substitutional phosphorous and bismuth in silicon and rare-earth ions in wide-bandgap semiconductors (e.g. cerium-doped yttrium aluminum garnet or Ce:YAG, praseodymium-doped yttrium orthosilicate or Pr: YSO; europium-doped yttrium orthosilicate or Eu:YSO; praseodymium-doped yttrium aluminum garnet or Pr: YAG, neodymium-doped yttrium orthovanadate or Ne:YVO, etc), most of which have been shown to spin polarize upon light excitation at room temperature. In one embodiment, the channel is provided in a layer of material that is adjacent the substrate. In another embodiment, the channel is formed in the substrate itself. The analyte may be introduced into the channel in a fluid, such as a liquid or a gas. In one embodiment, the channel is a microfluidic channel with a width between 1 micrometer and 100 micrometers. The microfluidic channel may have a depth of between about 100 to 300 nm. The channel has a length sufficient to permit contact with the channel surface for a sufficient amount of time to induce spin transfer when the analyte is moving through the channel at a predetermined flow rate. The channel may be made longer when faster flow rates are desired. Alternatively, the area in contact with the fluid can be enhanced by intercalating nanopillars or introducing surface roughness. A magnetic field is applied to break the symmetry in the color center-nuclear spin transitions. Depending on the application, the operating magnetic field may vary but a field strength of at 100 mT may be typical and the magnetic field may be applied by, for example, a permanent magnet.

In step 104, the defect centers are illuminated with light while the magnetic field is applied. The light wavelength and intensity is chosen to optimize the spin polarization of the color centers. For example, in the case of NV centers in diamond, one would use green illumination with intensities of order 5 mW per square micrometer. The illumination of the defect centers causes the spins of the defect centers in the substrate to become polarized.

In step 106, the aligned spins in the substrate are permitted to induce corresponding spin polarization in the analyte. Depending on the target spin system (e.g., electron, proton or other nuclear spin species) and the type of source defect (NV centers or other centers as listed above) one chooses the magnetic field so as to optimize the process of nuclear dynamic polarization. For example, for NV centers in diamond one would operate at about 100 mT for proton spins or at about 50 mT for electron spins. The process of target spin polarization is also optimized by engineering the defect centers proximate the surface of the substrate where the analyte will pass. In one embodiment, the defect centers are implanted within 10 nm of the surface of the channel. The surface concentration of the defect centers within the substrate are typically within a range of about $10^{12}$ per square centimeter.

In step 108, the analyte is detected by virtue of its polarized spin state. Conventional detection techniques may be used. For example, the analyte may be detected by nuclear magnetic resonance (NMR) by using radio waves to induce a spin flip. Subsequent relaxation of the spin emits radio-frequency which is subsequently detected, thereby permitting detection of the analyte. Examples of devices for performing method 100 are discussed elsewhere in this specification.

Figure 2A:
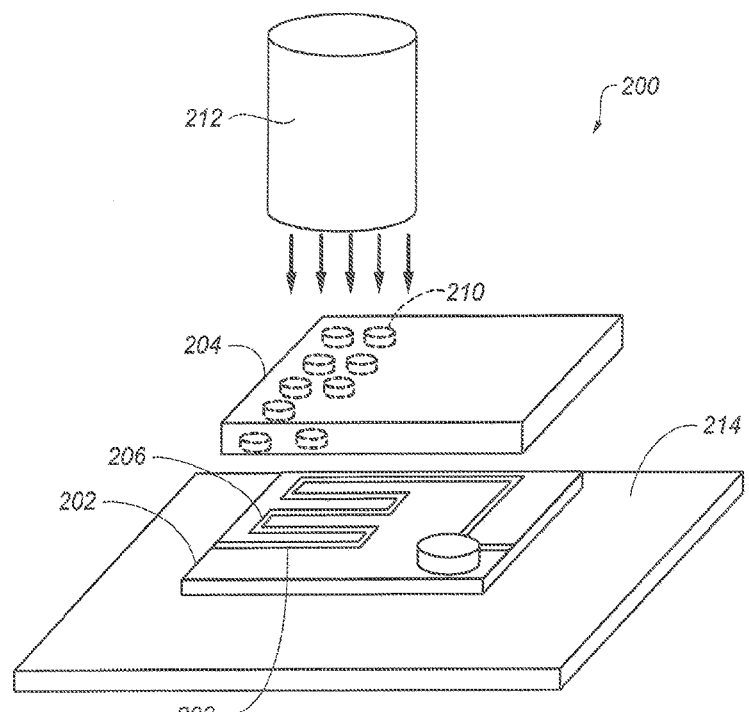
Figure 2B:
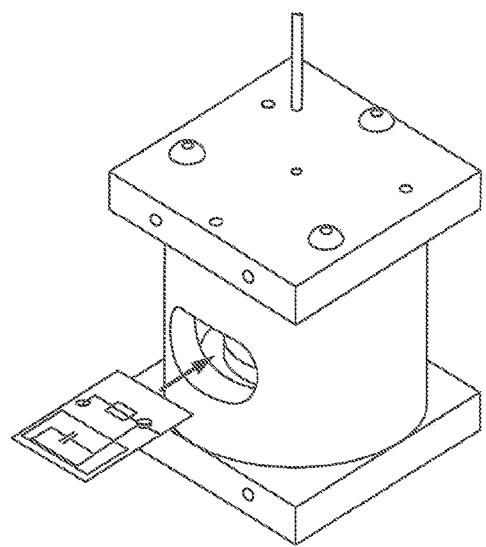
FIG. 2B depicts of insertion of the polarization system into a detection system.

FIG. 2A is a schematic depiction of a polarization system 200 integrating a substrate 202 and a single diamond crystal 204. A target fluid 206 circulating through a microfluidic channel 208 is exposed to optically pumped NV centers 210 implanted on a surface of the single diamond crystal 204 while being exposed to far-field illumination from light source 212. A magnet 214 provides an applied magnetic field $B_0$. For the sake of illustration, the substrate 202 and the single diamond crystal 204 are depicted as being spaced apart. In use, the substrate 202 and the single diamond crystal 204 are contiguous such that the target analyte 206 in the microfluidic channel 208 contacts the surface of the single diamond crystal proximate where the NV centers 210. In the embodiment of FIG. 2B, detection of the fluid polarization after circulation is carried out via inductively-detected NMR. In the embodiment of FIG. 2A, the microfluidic channel 208 is disposed within the substrate 202 such that at least three surfaces of the channel 208 are formed from the substrate 202 and a fourth surface of the microfluidic channel 208 is the surface of the single diamond crystal 204 with the NV centers 210.

The substrate 202 may be formed of, for example, a polymer such as polydimethylsiloxane (PDMS). In some embodiments, the substrate 202 is optically transparent such that photons emitted from the sample while within the microfluidic channel 208 may be received by a sensor. For example, the substrate 202 may be formed from an optically transparent material and/or be sufficiently thin (e.g. about 100 nm) to permit photons to leave the substrate 202. The substrate 202 need only be optically transparent over certain wavelengths, as determined by the wavelength of the photons of interest.

The single diamond crystal 204 comprises NV centers 210 that are implanted within 10 nm of the surface of the single diamond crystal 204 such that the target analyte 206 passes proximate the NV centers 210 as the target analyte 206 passes through the microfluidic channel 208.

In use, the target analyte 206 is passed through the microfluidic channel 208 as light from light source 212 is illuminated on the NV centers 210 disposed in the surface of the single diamond crystal 204. This illumination induces a large degree of spin alignment in the NV centers 210. As the target fluid 206 passes proximate the NV centers 210, this spin alignment is induced in the atomic nuclei and/or electrons in the target analyte. This induced spin alignment in the nuclei or electrons may then be sensed in a traditional manner (e.g. irradiation with radio waves and the like). For example, the system 200 may be inserted into a detector as shown in FIG. 2B. Unlike traditional approaches, the spins that are induced using the disclosed method have a greater degree of spin polarization, resulting in a more sensitive method.

Figure 3:
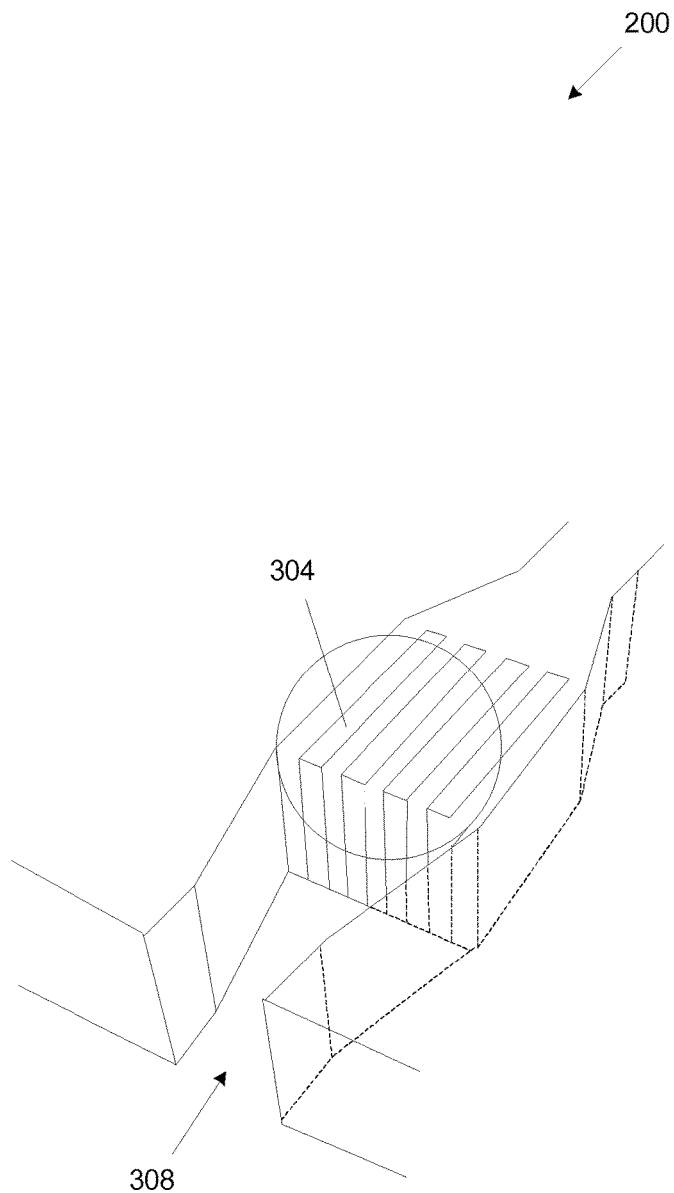
FIG. 3 is a schematic of a microfluidic channel of another embodiment of a polarization system.

FIG. 3 is a schematic depiction of a nuclear spin polarization system 300. A target analyte 306 circulates trough a microfluidic channel 208 and between closely spaced diamond walls 304 whose surfaces have been implanted with shallow NVs (not shown in FIG. 3). The NVs are, in one embodiment, disposed with 10 nm of the surface of the diamond walls 304.

In use, light from a light source is illuminated on the NVs in the diamond walls 304. The spins of the NVs achieve alignment. A target analyte passes through the microfluidic channel 308 while a magnetic field $B_0$ is applied and comes in contact with the now-polarized spins of the NVs and spin polarization is induced in the atomic nuclei and/or the electrons of the target analyte. This induced spin alignment may then be sensed in a traditional manner.

Theoretical Basis

Hyperpolarization involves the preparation of a (nearly) pure and easily replenishable quantum state (via optical absorption, for example), with concomitant coupling of that state to either nuclear or electron spin angular momentum. The technique has evolved through many disciplines to now include commercially available machines for delivery of hyperpolarized xenon gas (via optical pumping) and hyperpolarized solvents for analytical NMR (via dynamic nuclear polarization, DNP). Such machines are promising, yet their utility is confined to a limited class of problems (e.g. Xe gas) or require expensive and highly complex instrumentation (e.g. gyrotrons). The methods disclosed herein use a chemically stable, easily available, and deeply understood source material that obviates at least some of the shortcomings of the prior art. One such source material is diamond.

The nitrogen vacancy [NV-] color-center in diamond is a well-studied defect. The science that underpins this "artificial molecule" provides an opportunity to exploit a profound new type of optical pumping of spins. A fortuitous combination of electronic structure, intersystem crossing rates, and selection rules allows the [NV-] ground state spin-triplet (S=1) to completely convert into the $m_s=0$ magnetic sub-level upon optical illumination. The disclosed method makes this "hyperpolarized" quantum state of the [NV-] center the source for schemes to couple into nuclear, or other electron, spin states across the diamond interface to target solids, liquids and gases. Defects or impurities in SiC or Si and rare-earth ions in wide-bandgap materials, are also contemplated for use with the disclosed methods, and virtually all of the discussion regarding [NV-] applies to these other types of defects. Of particular note is the observation that two of the defects associated with commercially available HPSI 4H—SiC ("PL5" and "PL6") can be optically polarized at room temperature. Something similar can be said about Ce ions in YAG.

Specified quantum states within the diamond and related families of optically active defects were prepared. These quantum states may be coupled to other defects or proximal NMR-active nuclei (such as $^{13}C$). Various schemes were considered to transfer this polarization from optically active defects across interfaces. In addition to this "spin engineering," materials engineering was employed such that defects will be placed at locations appropriate for extending hyperpolarization across interfaces. Thus, the defect engineering and spin dynamics of flat diamond (and related materials) interfaces forms one body of work.

A second body of work focuses on microfluidics devices for directing unpolarized target analytes over polarized diamond and other interfaces. These interfaces are designed to optimize spin polarization transfer mechanisms and fluid flow through polarized or channels carved in diamond or related material platforms. An example of such a system would be microfluidic channel(s) etched from diamond and implanted with an appropriate number density of [NV-] or related defects. Finally, nano-sized crystals (e.g. nanodiamond) may be distributed in a packed-bed type arrangement to provide bulk quantities of hyperpolarized fluids. This device design is complicated by the lack of control over nanoparticle orientation with respect to optical excitation or applied magnetic fields. This complexity, however, also affords an opportunity to exploit different magnetic sub-levels other than the $m_s=0$ state of [NV-] diamond.

The antecedent for the delivery of hyperpolarization to arbitrary external systems is the generation of nearly pure quantum states at (or near) the host-target interface, then the transport of polarization across that interface to the target medium. Diamond single crystals were implanted with [NV-] and modeling was conducted to determine how and where defect centers are generated. These studies provide recipes for the placement of [NV-] centers at optimal locations and "per unit volume" concentrations. In parallel with these defect-engineering schemes optimal transfer of [NV-] pure state pumping into proximal electron and nuclear polarization within the diamond interface was studied. The transfer of that polarization across the flat interface to the target material was also engineered. These topics are described in more detail elsewhere in this disclosure.

Ion-implanted samples exhibit exceptional properties such as [NV-] lifetimes of 0.2 ms (or higher in $^{13}C$ depleted crystals). The distance to the surface can be accurately controlled by choosing adequate implantation energy, whereas the use of $^{15}N$ ions allows for easy discrimination from native defects (the triplet in the magnetic resonance spectrum of an [NV-] yields a doublet when $^{14}N$ (a spin-1 nucleus 99.6% abundant) is replaced by $^{15}N$ (spin-½)). In addition to conventional ion implantation techniques, Hydrogen annealing may also be useful as an additional procedure for modifying the "depth-distribution" of [NV-] centers. The "quantum fidelity" of these engineered interfaces may be assessed via Hahn Echo ODMR sequences to show coherences in the 0.1-0.2 ms range.

The [NV-] system is fascinating in that the dominant spin dynamics changes markedly when moving from high to low magnetic fields. In this latter regime, polarization transfer to nearby spins has been demonstrated by "tweaking" energy levels via small to modest Zeeman effects. In the absence of an applied magnetic field, the large [NV-] zero-field splitting creates an energy mismatch between the [NV-] and nearby spins, making spin flips energetically unfavorable. An external magnetic field (50 mT), however, can be used to bias the excited state triplet to a level anticrossing where the zero-field and Zeeman terms cancel, making the hyperfine coupling dominant and energetically allowing spin flips between the [NV-] and nearby spins. More advanced procedures, such as double resonance protocols that allow spin exchange via dressed states, can enable the transfer of polarization in the absence of strong magnetic fields. Other nuclei (C, N, H, etc.) are also contemplated for use with the disclosed methods.

There are several motifs for the transfer of polarization from diamond surfaces to target nuclei external to the diamond. These motifs were categorized into three classes: those governed by direct interactions between [NV-] and external nuclei, those that utilize $^{13}C$ nuclei hyperpolarization within "optically pumped" diamond, and those mediated by other paramagnetic centers at diamond surfaces. All three mechanisms are described in this disclosure.

The direct interaction between [NV-] centers and nuclei external to a diamond surface can be accomplished for example, by [NV-]-$^{1}H$ double resonance. Sensing of the resulting nuclear spin polarization can be carried out by using a more dilute set of NV centers as magnetic probes. In this latter case, spin noise fluctuations from protons external to the [NV-] may be detected in fluorescence.

The transfer of polarization from [NV-] to protons is accomplished in several ways. In one approach, small Zeeman fields are employed to adjust [NV-] energy levels. For example, applying an external magnetic field of about 500 G parallel to the [NV-] axis allows the hyperfine exchange terms in the [NV-] Hamiltonian to become dominant. Another class of experiments employ double resonance experiments to energy-match [NV-] states with protons in the rotating frame, an agenda that follows directly from Hartmann and Hahn.

Transfer from hyperpolarized $^{13}C$ nuclei at the diamond surface to mobile species provide another strategy for preparing finite volumes of highly polarized solvents.

The first generation of devices for delivering hyperpolarization from a source material (diamond, SiC, or wide-bandgap semiconductors) to target fluids employs microfluidics. To realize efficient spin polarization of a liquid for NMR studies, a diamond microfluidic device combines four sub-components: (i) fluid control, (ii) spin polarization in in the source material, (iii) spin transfer from the source to the fluid, and (iv) electronics for spin manipulation (and if necessary, readout) of the color center spin. If, for concreteness, we assume diamond as the source material, the central component of the microfluidic device is the "diamond spin-polarizer" (DSP), a diamond crystal engineered to host high density of NVs near the surface. Upon green light illumination NV centers in the DSP spin polarize and then transfer this polarization to a liquid via microfluidic interfaces consisting of deep channels etched into the diamond chip (see, for example, FIG. 2 or FIG. 3). The spin polarizer terminates in a microfluidic channel that leads to an NMR detection region on the chip. Micro-fabricated wires are integrated in the polarizer region to uniformly and precisely control the spin polarization within the diamond region. Microfabricated induction coils in the detection region of the microfluidics device serve to detect the polarization of the liquid. By using a multitude of microfabricated coils, it is possible to generate a wide range of magnetic field patterns and gradients.

In one embodiment, the spin polarizer's microfluidic channels are closely packed to maximize the surface area between the diamond and the fluid that is moving through the channels. Maximizing diamond surface-to-fluid volume is desirable since, regardless of which polarization transfer mechanism dominates, the coupling will scale as $1/R^3$. Thus the microfluidic device uses high aspect-ratio channels in diamond.

Fabrication processes for producing high aspect ratios in diamonds are known that use, for example, plasma etching. These processes enable the fabrication of thin, tall walls of diamond by vertically etching a commercially available high-purity single-crystal diamond plate. To produce slabs that are nearly vertical and deep, a process that alternates between plasma etching and mask deposition steps may be used, similar to the Bosch process used in deep reactive ion etching. This process enables vertical nano-slabs with aspect ratios (height/thickness) of about 50, including 200 nm thick nano-slabs that are 10 micrometers deep.

The vertical slabs are embedded with [NV-] centers in a variety of ways. If constructed of high-purity diamond with a N-defect concentration near 10 parts per million (ppm), the limiting 'reagent' in the [NV-] generation process is the vacancy. Vacancies may then be created by high-energy electron irradiation of 3.5 MeV or with 100 keV $He^{2+}$ ion irradiation. The samples are then annealed at 800° C. for several hours to liberate vacancies, which preferentially bind to N atoms. Because high electron and $He^{2+}$ energies are used, [NV-]s are created throughout the volume of the diamond sample. It is noteworthy, however, that the relative abundance of N centers may actually be beneficial for spin transfer.

If the diamond substrate is made of ultra-high-purity diamond with an N-defect concentration of 10 ppb or less, it may be desirable to implant both N atoms and vacancies. Efficient [NV-] generation may be provided by implantation of $^{15}$N at varying depths, using different acceleration energies that yield a mean depth of one nanometer per keV of acceleration energy. In those situations where the vacancies are still too sparse and not co-located well with the N stopping range, then additional implantation of $^{12}$C or $He^{2+}$ may be performed to create vacancies at the desired depth. It may be desirable to create [NV-] centers throughout the vertical slabs. In these ultra-high-purity diamond samples, repeated $^{15}$N implantation at a range of energies from about 5 keV to about 1 MeV may be desirable. The diamond sample may be positioned at a slight angle with respect to the ion beam to create [NV-]s in the surface of the vertical diamond membranes.

Fluid dynamics poses some additional challenges, since laminar flow of solvent through the diamond channels could potentially result in poor overall spin polarization as the central solvent current would have little contact with the spin-polarized diamond wall and hence experience only slow spin polarization. Care should be taken to reduce laminar flow and increase turbulent flow. In one embodiment, the aspect ratio is developed to fabricate walls with a spacing down to 140 nm and thickness down to 80 nm, while maintaining a 10 micrometer depth, to improve the spin transfer interface region.

Other paramagnetic defects in diamond can effectively increase the polarization density of the diamond. Although these "dark spins" do not have the optical pumping properties that make the [NV-] attractive, they can serve as effective "amplifiers" that increase the overall polarization because they are influenced by nearby [NV-]s. In addition, since electron-electron dipole coupling is strong compared to nuclear-electron coupling, the interaction of [NV-]s with these defects occurs over longer length scales. Consequently, these defects may serve to transfer the polarization of bulk [NV-]s to spins far from the diamond surface.

The disclosed methods provide the ability to polarize protons in water to about 0.1% or more, representing at least a 100-fold improvement over what is possible with the world's most powerful NMR magnets.

Nanodiamond-based Dynamic Nuclear Polarization

In one embodiment, the fluid is injected through a porous gel (such as those used in commercial filtration matrices) whose inner surface has been coated with engineered diamond nanocrystals. This nano-crystalline diamond structure provides an alternative to the microstructured single-crystal diamond. Compared to single-crystal diamond, the higher surface-to-volume ratio ensures a better contact between the fluid and the diamond. However, because the nanocrystals (and thus the [NV-] symmetry axes) become randomly oriented in this device, only a small fraction of [NV-]s can be properly manipulated, a limitation that makes [NV-] optical pumping not necessarily the best strategy to polarize a target fluid.

Unlike the nitrogen-vacancy center, the typical paramagnetic defect in nanodiamond is optically inactive (and thus cannot be polarized by visible illumination). However, while [NV-]s are normally absent in small diamond particles, other defects (such as those formed by surface dangling bonds or substitutional nitrogen) can be quite abundant and thus serve as an appealing resource for DNP experiments. Indeed, dynamic nuclear polarization using silicon nanoparticles has been demonstrated recently, but good polarization efficiency could only be attained at low temperatures, mainly due to the poor spin relaxation characteristics of the paramagnetic defects active in these particles. In the disclosed methods a much more controlled (and favorable) scenario is provided, particularly given the possibility of nanoparticle engineering, and the ability to gather relevant information on the dark-spin ensemble beforehand, even at the level of a single nanoparticle. For example, a double resonance protocol may be implemented in which the response to a Hahn echo sequence from a single [NV-] is monitored as simultaneous microwave of variable frequency are applied using a second control channel. The [NV-] echo signal drops as a dark-spin resonance is crossed, thus allowing indirect reconstruct the spin-bath EPR spectrum from an individual nanoparticle. For this particular case, a detailed examination shows that a major fraction of the spin bath (50-70%) is formed by substitutional nitrogen (a spin-½ defect) with a number concentration on the order of a few hundred parts per million. An important contribution is also found from surface defects, likely dangling bonds. Remarkably, these defects have a narrow frequency distribution corresponding to a well-defined g-factor of approximately two and share with the nitrogen ensemble a common coherence and spin-lattice relaxation time (of order 0.6 is and 0.5 ms, respectively).

Compared to the typical DNP experiment in a fluid—often exploiting the nitroxyl radical from molecules in solution such as TEMPO—the use of engineered diamond nanocrystals has several important differences. For one, nitroxyls cannot be polarized optically so in this case radio-frequency or microwave is used to saturate spin transitions. This operation results in an enhancement of the target spin system but the enhancement is comparatively lower than that possible with NV centers. Further, paramagnetic centers resulting from near-surface defects are not necessarily affected by hyperfine splittings (since 99% of the carbon matrix is spin-less), implying that multiple transitions can be irradiated simultaneously. This situation is in contrast with that found in nitroxyls, where only one of the three possible transitions is typically excited, thus leading to an effective enhancement factor of about one third the maximum possible. The concentration and class of defects in the nanocrystal can be engineered by adequately selecting the type and intensity of the high-energy beam during sample preparation (e.g., exposure to an electron beam will create less crystal damage than irradiation by heavier ions) and the final number of surface defects can be further controlled via surface termination. Also, because the diamond nanoparticle is attached to the matrix surface, it does not contaminate the target fluid in any way. Because diamond nanocrystals are non-cytotoxic and largely biocompatible, it is possible to envision multiple extensions where the nanocrystal is embedded within the system under investigation (e.g., a cell), either to induce nuclear spin polarization in situ, or to introduce various forms of imaging contrast.

Figure 4A:
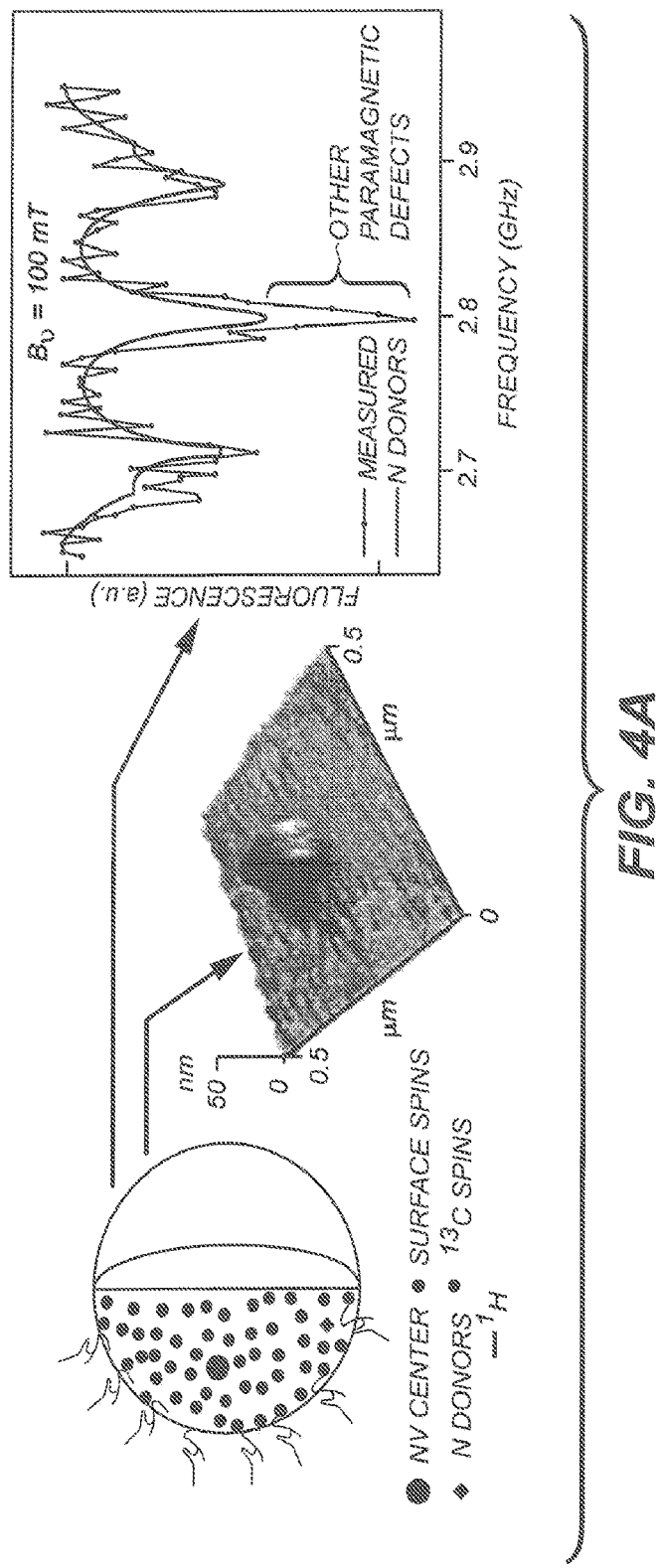
FIG. 4A depicts an individual diamond nanoparticle.

FIG. 4A depicts a composition that has the ability to dynamically transfer polarization from an [NV-] spin to surrounding paramagnetic centers in an individual diamond nanoparticle. In the embodiment of FIG. 4A, a nano-sized diamond substrate is surface implanted with at least one NV center. The surface may also be enriched for C-13 and functionalized with N donors. FIG. 4A shows the AFM image and the NV-detected spectrum of paramagnetic centers in the individual nanocrystal. The black solid line is the calculated response for nitrogen donors. In this example a Hartman-Halm protocol is used where both the [NV-] and dark spins are subjected to resonant pulses of microwave excitation of the exact same amplitude. While energy mismatch generally prevents flip-flops between different spin species in the lab frame, polarization can be transferred in the rotating frame when the amplitudes of the two simultaneous microwave fields are chosen to produce equal Rabi splittings. An interesting feature of this approach is that it allows not only to dynamically pump the bath polarization but also to simultaneously probe the level of polarization attained, at least in the [NV-] vicinity. For this purpose, a spin transfer blockade is used, i.e., the idea that spin transfer from the [NV-] into the bath is partly inhibited when neighboring spins are already polarized.

Figure 4B:
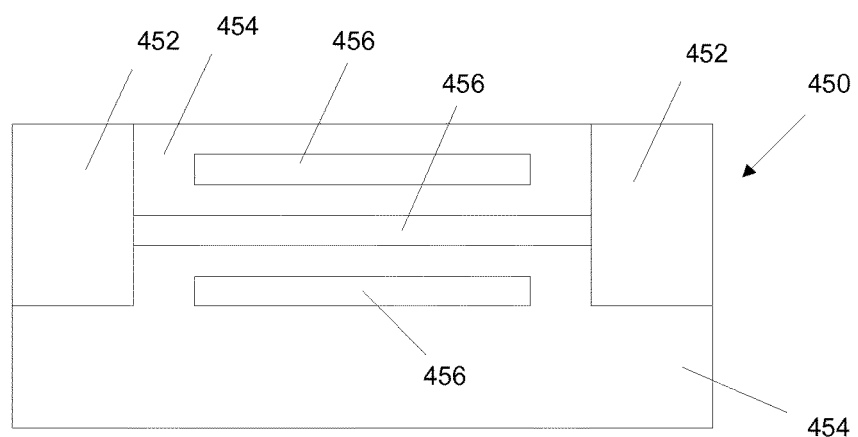
FIG. 4B is an embodiment of a semiconductor device made using NV centers.

FIG. 4B depicts a device 450 with geometry similar to that used to fabricate diamond-based FET transistors. A pair of electrodes 452 (e.g. boron-doped electrodes) injects carriers into the boron-delta-doped layer. Layers of NV-rich diamond 456 separated from the boron layer by intrinsic diamond are also created. The NV-rich layers are spin polarized upon exposure to light. When carriers circulate through the boron-doped layer, spin relaxation caused by interactions with neighboring NVs lead to carrier spin polarization.

In FIG. 5A-D this concept is experimentally demonstrated by increasing the time interval separating consecutive applications of the Hartman-Hahn sequence (triangles in FIG. 5C). Spin diffusion and relaxation during the extra time reduces the average dark spin polarization in the nanocrystal, hence bringing the equilibrium [NV-] signal nearer to zero. A more detailed examination shows that at optimum pumping conditions the dark spin bath polarization reaches approximately 50% in the vicinity of the [NV-], and averages about 5% throughout the nanocrystal volume, a promising result for a room-temperature experiment.

Besides polarizing electronic spins, the Hartman-Hahn protocol can be adapted to transfer polarization to nuclear spins as well. Given the large differences between the electronic and nuclear gyromagnetic ratios (typically exceeding three orders of magnitude), energy matching in the rotating frame is impractical. This problem, however, can be circumvented by a hybrid, laboratory/rotating frame matching in which the amplitude of the electron spin-locking microwave is chosen to produce an energy splitting coincident with that induced on the nuclear spins by the static magnetic field. Such strategy has already been used extensively to dynamically polarize $^{13}$C spins in bulk diamond with large nitrogen content and, more recently, in high purity crystals using optically pumped [NV-]s. Naturally, the same principles can be extended here to polarize nuclei other than $^{13}$C, a tantalizing possibility made all the more plausible by the already mentioned demonstration of proton spin detection using shallow [NV-]s.

Nuclear Spin Polarization via Paramagnetic-center-induced Relaxation

The spin of such centers can serve as a versatile nanoscale probe, capable of detecting, for example, the nuclear spin field created by molecules on the diamond surface. This specification discloses a complementary application where, rather than acting as a sensor, the NV is engineered and manipulated to serve as the source of nuclear spin relaxation. For shallow NVs continuously pumped into a pre-defined spin state, we show that the magnetic fluctuations arising from molecular surface hopping drive adsorbed nuclear spins into a quasi-equilibrium state of athermal polarization. The sign and amplitude of this polarization is a sensitive function of the NV depth and surface geometry. In particular, nanoscale roughness at the interface separating the NVs from the adsorbed molecules plays a key role in making nuclear spin relaxation sufficiently strong. For a given surface topology, the resulting nuclear magnetization changes sign as we gradually displace the NVs towards the diamond surface. Using microfluidic modeling it is shown that substantial nuclear spin polarization can be attained by flowing the molecules of a gas or a liquid across an optically pumped diamond nanostructure. The technique may be referred to as NV-driven dynamic nuclear polarization or NV-DNP.

To model the dynamics of spin relaxation between paramagnetic centers and nuclear spins in a fluid we start by considering the 'diamond spin pump' geometry of shallow NVs within a source diamond crystal. The NVs are continuously driven into the state $m_S=0$ of the NV ground state triplet via green light illumination. A dc magnetic field B normal to the crystal surface and coincident with the NV symmetry axis breaks the degeneracy between the $m_S=\pm 1$ states. A microfluidic structure brings the molecules of a target gas or liquid in contact with the source crystal. A fraction of these molecules is temporarily adsorbed onto the diamond surface causing a dipolar magnetic interaction with the NVs. As molecules sample different positions within the surface, this interaction randomly evolves in time with a characteristic correlation time $\tau_c$. For a sufficiently dilute collection of NV centers the dynamics can be simplified to that of individual spin pairs, in the present case formed by an NV and a nuclear spin $I=\frac{1}{2}$.

Ignoring for now molecular exchange with the bulk of the fluid, detailed balance between the populations in the different energy levels yields the steady-state polarization of adsorbed nuclear spins $$P_I^{(a)}(m_S=0) \cong -\frac{(W_2-W_0)}{\left(W_2+W_0+\frac{1}{T_{1I}^{(a)}}\right)}, \qquad (2)$$

where $1/T_{1I}^{(a)}$ is the nuclear spin relaxation rate on the diamond surface due to processes other than the interaction with the NVs. In the above expression the transition rates have the form $$W_j = \frac{\xi_j \tau_c}{1+((\omega_{NV}^{(-1)}-(-1)^{j/2}\omega_I)\tau_c)^2}$$

for j=0, 2 with $\tau_c$ denoting the correlation time of the adsorbed molecules; $\omega_I=\gamma_I B$ is the nuclear Zeeman frequency, $\omega_{NV}^{(-1)}=|\omega_{crys}-|\gamma_S||B|$ is the $m_S=0\to m_S=-1$ NV transition frequency with $\omega_{crys}=2\pi\times 2.87$ GHz, the zero field splitting of the NV ground state, and $\gamma_I(\gamma_S)$ denotes the nuclear (electronic) spin gyromagnetic ratio. Eq. (2) is a simplified expression approximately valid when $\tau_c>0.2$ ns and B>30 mT which are typical conditions; a formula valid for all correlation times and magnetic fields can also be derived. $\xi_j$ with j=0, 2 are constants quantifying the efficiency of the NV-induced nuclear spin relaxation, which depends strongly on the geometry governing the interaction between the NV and adsorbed nuclear spins. If the crystal is flat on a scale much larger than the NV distance to the surface (referred to as case (i)), a calculation assuming dipolar coupling shows that $\xi_0^{(i)} = \xi_2^{(i)} \cong 0.19\chi$, where $$\chi \equiv \frac{\pi\hbar^2 k^2}{Az^4},$$

z is the NV distance to the surface, $k \equiv \Xi_0 \gamma_I \gamma_S/4\pi$, and $1/A \equiv \sigma$ is the NV surface density. Since typically $\omega_{NV}^{(-1)} \gg \omega_1$, $W_2$ and $W_0$ converge to similar values so that the steady state polarization, proportional to the difference between the two, is greatly diminished. This cancellation is a fortuitous consequence of the angular dependence governing the spin dipolar interactions between the NV and adsorbed nuclei, and can be altered by changing the system geometry.

Figure 6A:
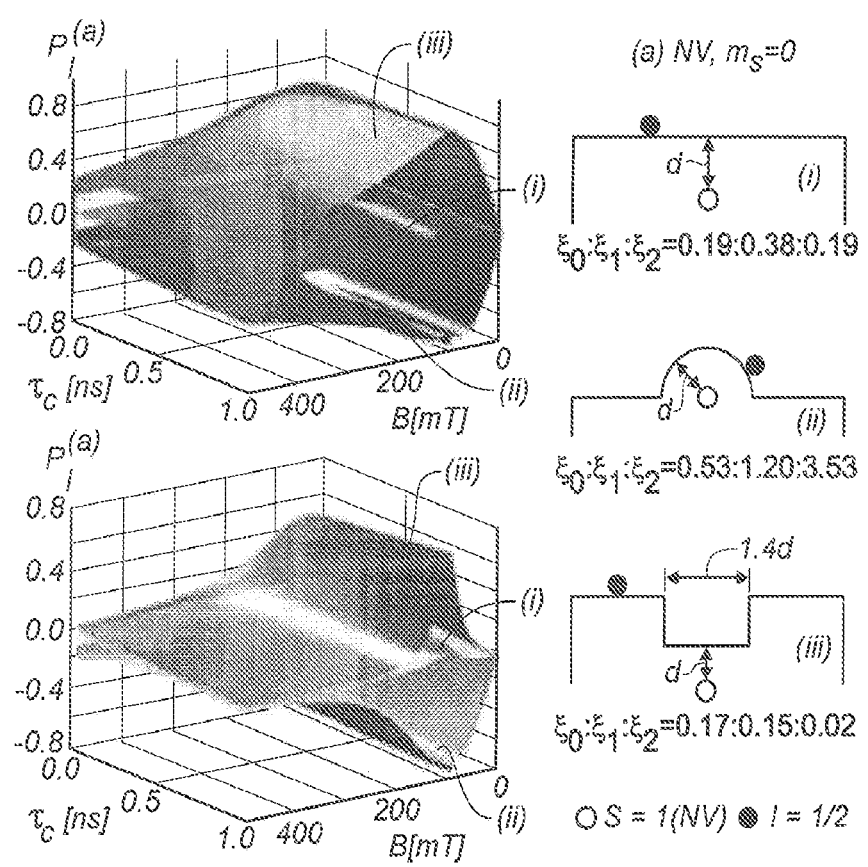
FIG. 6A, FIG. 6B and FIG. 6C depicts graphs showing polarization of absorbed spins as a function of the applied magnetic field and correlation time where the NV is below a flat surface, a dome and a cylindrical pit, each at different $m_s$ values.

One possibility is to align the magnetic field with the NVs whose axes are not perpendicular to the crystal surface. Here, however, we are particularly interested in the effect of surface topology: In FIG. 6A $P_I^{(a)}$ ($m_S = 0$) is plotted as a function of the applied magnetic field B and correlation time $\tau_c$ for three different configurations, where the NV is below a flat surface (case (i)), a dome (case (ii)), or a cylindrical pit (case (iii)). For simplicity, the top set of curves corresponds to the case where $1/T_{1I}^{(a)} \sim 0$.

FIG. 6A shows a remarkable change in the polarization amplitude and a sign reversal as the diamond surface evolves from a convex to a concave geometry (cases (ii) and (iii), respectively). The maximum nuclear spin order is attained near $B_c = 100$ mT, where $\omega_{NV}^{(-1)}$ is minimum, but substantial levels of nuclear polarization persist over a broad range of magnetic fields and correlation times. Level-anticrossing effects near $B_c$—not contemplated here—may lead to localized deviations from the presented model. These, however, are restricted to a narrow interval (of order ±5 mT or less in $^{13}$C-depleted diamond) and will be ignored throughout the remainder of the text.

In practice, adsorbed nuclear spins simultaneously experience multiple relaxation mechanisms, most importantly due to interactions with other, unpolarized paramagnetic centers within the diamond crystal. To assess the influence of these mechanisms on the adsorbed nuclear spins $P_I^{(a)}$ ($m_S = 0$) was recalculated in the case where $1/T_{1I}^{(a)}$ takes the value comparable to $(W_2 + W_0)_m$, where the subscript references the maximum NV-induced relaxation rate (bottom set of curves in FIG. 6A). We find that the polarization buildup is now restricted to a narrower range of magnetic fields, the effect being substantially more pronounced for the concave geometry (case (iii)). The latter is a direct consequence of the comparatively weaker NV-induced relaxation in this configuration: A direct calculation shows that the constants governing the transition probability amplitudes in a pit-like geometry are respectively given by $\xi_0^{(iii)} = 0.17\chi$ and $\xi_2^{(iii)} = 0.02\chi$. By contrast, a convex topology in the form of a dome yields $\xi_0^{(ii)} = 0.53\chi$ and $\xi_2^{(ii)} = 3.53\chi$. Therefore, and while the ratio $$\left|\frac{\xi_2 - \xi_0}{\xi_2 + \xi_0}\right| \sim 0.75$$

is comparable in both instances, the values $|\xi_2 \pm \xi_0|$ are approximately 20 times greater in case (ii), making this convex geometry less sensitive to other, coexisting paths of nuclear spin relaxation.

Although our discussion so far has been restricted to the case where the NV is selectively pumped into $m_S = 0$ of the ground state triplet, it is interesting to consider an alternate scenario where the NV population is steadily driven into, e.g., $m_S = -1$. Experimentally, this could be accomplished by concatenating intervals of laser excitation with selective microwave inversion pulses on a sufficiently fast time scale. Detailed balance yields in this case $$P_I^{(a)}(m_S = -1) = \frac{(W_2 - W_0)}{\left(W_2 + 2W_1 + W_0 + \frac{1}{T_{1I}^{(a)}}\right)}, \quad (3)$$

with $$W_1 = \frac{\xi_1 \tau_c}{1 + (\omega_I \tau_c)^2}.$$

By the same token and assuming selective NV pumping into $m_S = +1$, we obtain $$P_I^{(a)}(m_S = +1) = -\frac{(\tilde{W}_2 - \tilde{W}_0)}{\left(\tilde{W}_2 + 2W_1 + \tilde{W}_0 + \frac{1}{T_{1I}^{(a)}}\right)}, \quad (4)$$

where $$\tilde{W}_j = \frac{\xi_j \tau_c}{1 + ((\omega_{NV}^{(+1)} - (-1)^{j/2} \omega_I) \tau_c)^2}$$

with $j = 0, 2$ and $\omega_{NV}^{(+1)} = \omega_{crys} + |\gamma_S|B$. A plot of Eqs. (3) and (4) as a function of the magnetic field and correlation time is presented in FIB. 6B for the geometry of case (ii) and in the absence of intrinsic nuclear spin relaxation ($1/T_{1I}^{(a)} \sim 0$). Relative to the top set of curves in FIG. 6A, we observe major changes in $P_I^{(a)}$ including a sign reversal and a redistribution of the nuclear spin polarization into a narrower range around $B_c$ (for NV pumping into $m_S = -1$) or toward shorter correlation times (when $m_S = +1$). The overall conclusion is that NV pumping into $m_S = 0$ is not only the simplest way to induce nuclear spin alignment, but presumably the most efficient.

Figure 6B:
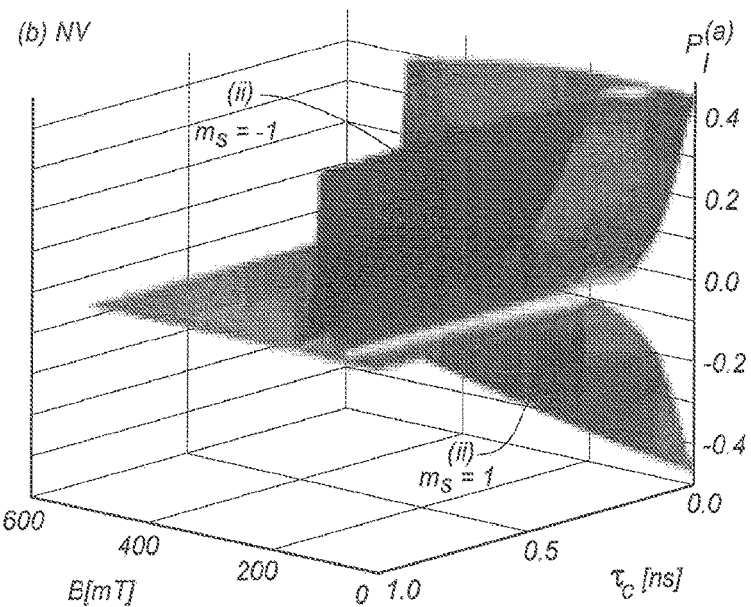
Figure 6C:
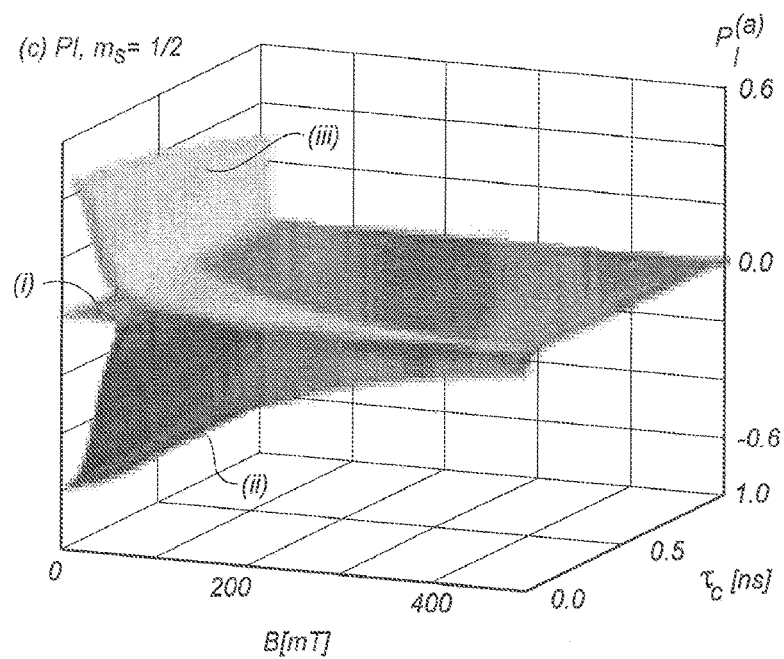

It is of interest to study closely the influence of other paramagnetic defects on $P_I^{(a)}$. Particularly important is the role of substitutional nitrogen (also called P1 center), a paramagnetic impurity (PI) of spin number ½: Because most NV conversion protocols have only a fractional yield, nitrogen impurities are present in all NV-doped surfaces, typically at a higher concentration. Conceivably, P1 centers can be dynamically polarized via contact with optically pumped NVs, and thus can themselves contribute to aligning adsorbed nuclear spins. FIG. 6C shows the predicted nuclear spin polarization for a model where nuclear spin relaxation is governed by spin-½ paramagnetic centers polarized to $m_S = +½$. Not surprisingly, we find a dependence on the surface topology comparable to that of FIG. 6A; due to the absence of a crystalline field, however, dynamic nuclear polarization is restricted to comparatively shorter correlation times and lower magnetic fields. This behavior is of interest not only when paramagnetic impurities drive nuclear alignment but, perhaps more importantly, when unpolarized PIs compete against polarized NVs. In this latter case, we model the relaxation rate of adsorbed nuclei as $(1/T_{1I}{}^{(a)}) \sim (W_2 + 2W_1 + W_0)^{(PI)}$ where the superscript indicates that the transition probabilities are those due to a spin-½ paramagnetic defect. Because of the distinct dependence on $\tau_c$ and B, the polarization loss—captured by the factor $[T_{1I}{}^{(a)}(W_2 + W_0{}^{(NV)})]^{-1}$—can be mitigated via an adequate selection of the working conditions (i.e., magnetic field, temperature, surface roughness, etc). In other words, the detrimental effect of unpolarized PIs on the dynamical polarization of adsorbed nuclear spins can be significantly suppressed, even for comparatively greater concentrations of paramagnetic defects.

A question of practical importance in the implementation of NV-DNP is how to best engineer the surface topology. From the results in FIG. 6A, FIG. 6B and FIG. 6C, we surmise that a convex geometry is among the most favorable, but arraying a set of NV-hosting, nanometer-sized domes is challenging with present technology.

We model an arguably more realistic scenario where engineered NVs occupy random positions across a horizontal plane of arbitrary height z along the surface normal; with this assumption, a smaller fraction of the plane becomes available to the NVs as z becomes greater than $z_{min}$, the height at the deepest valley point. Such configuration could be attained, for example, by controllably etching the surface of a delta-doped diamond. For the present calculations we assume that the roughness amplitude along the surface normal amounts to 5 nm (and choose the reference frame so that $z_{max} = 5$ nm and $z_{min} = 0$ nm). To account for the deleterious effect of bandgap-bending, we also assume that the NVs become inactive once the distance to the surface falls below 0.7 nm.

Figure 6D:
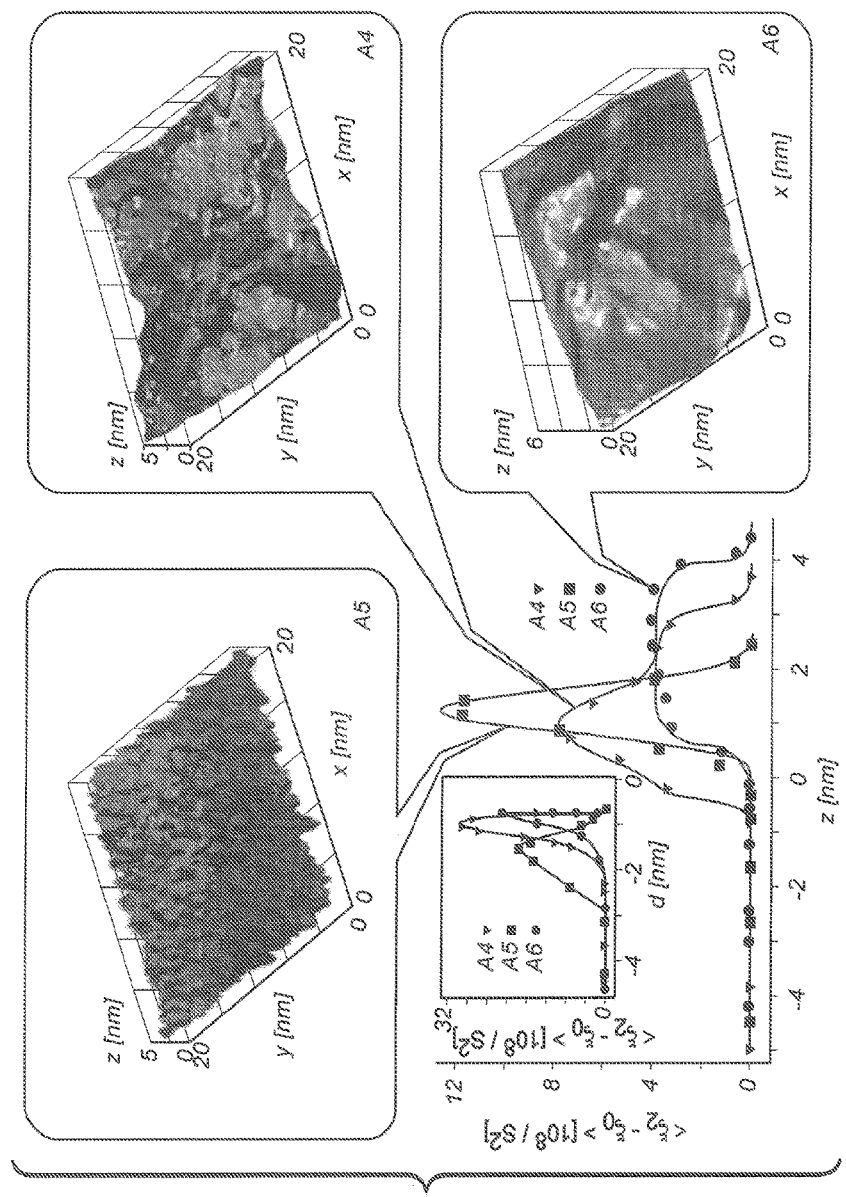
FIG. 6D depicts surface roughness of select samples.

Provided complete optical pumping of the NV into the $m_S = 0$ state, we obtain a direct measure of the nuclear spin polarization efficiency via $\xi_2 - \xi_0$—the difference between transition rate constants—which we calculate as the NV position is varied across a given horizontal plane at a fixed height z. See FIG. 6D. For NVs deep below the diamond surface (i.e., when z<0), we find that $\xi_2 - \xi_0$ closely follows the surface topography. This can be most clearly seen by considering a map at $z = -3$ nm, where $\xi_2 - \xi_0$ takes negative values below the valleys but turns positive underneath the crests (geometries corresponding to cases (iii) and (ii) in FIG. 6A, respectively). Overall, the average $\langle \xi_2 - \xi_0 \rangle$ over the entire plane is negative below z=0 because NVs are preferentially closer to nuclear spins in the surface valleys. As the NV depth is increasingly reduced, $\xi_2 - \xi_0$ preferentially turns to positive, resulting in positive averages when z>0 (main plot). The change is abrupt and takes place on a scale of just about 3 nm. An identical trend was observed after replacing the model surface by other similar code-generated surfaces implying that the calculated averages are representative of this type of surface as a whole. Interestingly, the positive section of the calculated curve (with maximum at $z \approx 2$ nm) completely dwarfs the negative tail (with minimum at $z \approx -1$ nm), which we interpret as a direct consequence of the greater values adopted by $\xi_2 - \xi_0$ in a convex geometry and near hillsides and cliffs. The latter is implicit in a maps of $\xi_2 - \xi_0$ at z>0, where we observe large, positive contributions (i.e., sections where the NVs collapse due to proximity to the surface).

The predominant configuration between shallow NVs and adsorbed nuclei (and thus the range and maximum amplitude of $\langle \xi_2 - \xi_0 \rangle$) may be controlled by the experimenter through an adequate selection of the roughening protocol. This is shown in by, for illustration purposes, calculating $\xi_2 - \xi_0$ for three new code-generated surfaces. The roughness amplitude is chosen to be 5 nm but the code is modified to alter the frequency and spread of the valleys and crests throughout the surface. We find that $\langle \xi_2 - \xi_0 \rangle$ reaches a higher maximum when the surface is comparatively more rugged. The positive section of the curve, however, spreads over a narrower range, which, in practice, would make this topography more susceptible to NV misplacement. We observe the exact opposite as we generate smoother-looking surface features, with a mesa-like behavior emerging.

Whether to introduce surface roughness before or after NV implantation is a decision likely to be influenced by a number of factors throughout the various surface preparation steps. Material processing considerations notwithstanding, the answer is not obvious when the analysis is restricted to the surface topology: When the NVs are distributed over a horizontal plane (as assumed thus far), deep surface roughening selectively removes the color centers near the valleys (where $\xi_2 - \xi_0$ is negative), presumably leading to stronger NV-DNP. This argument may be deceiving: The value $\langle \xi_2 - \xi_0 \rangle$ may be recalculated for the same three model surfaces. Unlike the main plot, we assume this time that the NVs have been implanted at a uniform depth d relative to the local height $z(x, y)$ of the roughened diamond surface. We find a remarkable change in the overall behavior towards a sharper dependence on NV position and higher maxima. We observe a reversal of the trend in the main plot, with more coarsely grained surfaces leading to greater $\langle \xi_2 - \xi_0 \rangle$ values.

NV surface density and implantation depth are additional practical facets worth considering in some detail. NV centers engineered as close as 1 nm from the surface have been shown to retain the relatively long coherence lifetimes required for spin sensing. Similar fabrication protocols could be adapted to the present application so as to create dense layers of near-surface NVs. We emphasize, however, that the spin-lattice relaxation times $T_{IS}$ governing the NV dynamics (typically 100 microseconds in nanocrystals and up to 10 ms in high-purity bulk crystals) need only be longer than the correlation time $\tau_c$ characterizing molecular hopping on the diamond surface (anticipated to be much shorter, see below). Thus, NV surface densities exceeding $10^{12}$ cm$^{-2}$ at a depth of 1-2 nm below the surface are realistic in the present application without any immediate deleterious effect.

The numerical modeling of the nuclear spin polarization of a fluid partly relies on the assumed correlation time, which depends on the physics governing the dynamics of the target molecules near the diamond surface. Adsorbed molecules in gases, for example, hop from one site to the next during a dwell time $\tau_a \gg \tau_c$ until finally desorbing from the surface. The fractional time $f = \tau_a / \tau_b$, that a molecule spends on the solid relative to the time $\tau_b$ in the bulk of the fluid is a thermally activated function that depends on the surface potential (and thus on the surface roughness and termination) of the particular solid surface under investigation. This type of dynamics is observed, e.g., in the study of optically-pumped alkali vapors, where the correlation time $\tau_c$—in this case governing the interaction of nuclear spins in the vapor with paramagnetic defects on the surface of the glass container—can be quite long for typical operation conditions.

The dynamics of molecules at a solid-liquid interface are less understood: Several studies have demonstrated how solids induce order in adjacent fluids but various boundary conditions are invoked, ranging from the no-slip condition—where the liquid is static relative to the solid at the surface—to pure slip, to multi-layer locking. We assume that the relevant processes at the solid-liquid interface can be described via an effective correlation time $\tau_c \geq 0.1$ ns. This assumption is justified by noting that for NVs sufficiently close to the surface, the unit time probabilities $W_j \propto 1/z^4$ are non-negligible over a range of a few nanometers, where the dynamics transitions from quasi-static (on the surface) to mobile (in the fluid). Note that determining the exact correlation time is largely unnecessary since, as shown in FIG. 6A, FIG. 6B and FIG. 6C, the steady-state nuclear spin polarization is rather insensitive to $\tau_c$ (at least for $\tau_c \geq 0.1$ ns). By the same token, our formulas are valid regardless the type of trajectories molecules follow on the surface (e.g., discrete or continuous hops), and thus are applicable to both liquids and gases.

Building on the above considerations, we now proceed to model the dynamic polarization of a bulk fluid brought in close proximity with shallow NVs optically-pumped into $m_S=0$. FIG. 7A introduces a possible geometry: A microfluidic channel steers the target liquid or gas into an optically-pumped diamond microstructure formed by two parallel diamond walls separated by 0.5 micrometers. We assume that the NV depth and nanoscale roughness of the diamond surface is chosen to optimize $\langle \xi_2 - \xi_0 \rangle$. To model spin transport in the microfluidics structure, we first note that the diffusion time across the width $z_w = 500$ nm of the channel for a fluid such as water is $\tau_w = z_w^2 / D = 109$ microseconds (the self-diffusion coefficient for water is $D = 2.3 \times 10^{-9}$ m$^2$/s). Since arguably $\tau_w \ll |W_2 \pm W_0|^{-1} < T_{1I}^{(b)}$ we look for solutions where the proton polarization $\langle I \rangle (z, y, t) \approx \langle I \rangle (y, t) \equiv 1/z_w \int_0^{z_w} \langle I \rangle (z, y, t) dz$ is independent of z. In this limit the spin transport equation for NVs pumped onto $m_S=0$ in a magnetic field B=110 mT reduces to:

$$\frac{d\langle I \rangle}{dt}(y, t) = -\langle I \rangle(y, t) \left( \frac{1}{\hat{T}_{1I}^{(NV)}(y)} + \frac{1}{T_{1I}^{(a)}(y)} + \frac{1}{T_{1I}^{(b)}} \right) - \frac{\langle S_0 \rangle}{T_{1I}^{(NV)}(y)} - \frac{2v}{3}\frac{\partial \langle I \rangle}{\partial y}(y, t) + D \frac{\partial^2 \langle I \rangle}{\partial y^2}(y, t), \quad (5)$$

where $1/T_{1I}^{(NV)} \approx f_{eff}(W_2-W_0)|_{z_0} \theta(|\gamma|-\gamma_I/2)$, $1/\hat{T}_{1I}^{(NV)} \approx f_{eff}(W_2+W_0)|_{z_0} \theta(|\gamma|-\gamma_I/2)$, $1/T_{1I}^{(a)} \approx f_{eff} W^{(PD)} \theta(|\gamma|-\gamma_I/2)$, $\theta(y)$ is the Heaviside function, $z_0$ is the NV distance to the surface, $$f_{eff} = \frac{2z_0}{3z_w}(1 - z_0^3/(z_w+z_0)^3)$$

is the effective fraction of molecules in contact with the surface, $2v/3$ is the average velocity across the channel, and we have chosen the origin of the reference frame to coincide with the midpoint of the implanted section of the channel, of length $y_I$. We solve Eq. (6) and determine the bulk fluid polarization $P_I^{(b)}(y, t) \equiv 2 \langle I \rangle(y, t)$ numerically using finite-difference forward integration over a large domain L in y to approximate boundaries at infinity. The results for $P_I^{(b)}(y, t)$ near the NV rich central region with $\langle S_0 \rangle = \frac{1}{2}$, $z_0 = 1$ nm, $y_I = 50$ micrometers, L=1.6 mm, $f_{eff} = 1.3 \times 10^{-3}$, $T_{1I}^{(b)} = 10$ s, $W_2|_{z_0} = 1$ s$^{-1}$, $W_0|_{z_0} = 0.15$ s$^{-1}$, and $W^{(PD)} = 1$ s$^{-1}$ at two flow velocities $v = y_I/T_{1I}^{(b)} = 5$ micrometers/s and $v = 10 \, y_I/T_{1I}^{(b)} = 50$ micrometers/s are shown in FIG. 7B. The limit steady-state polarization possible in a channel whose length L coincides with the length of the implanted section $y_I$ is $(P_I^{(b)})_{lim} = -f_{eff}(W_2-W_0)/(f_{eff}(W_2+W_0+W^{(PD)})+1/T_{1I}^{(b)}) \approx -1.1\%$, which is roughly a factor of six larger than the maximum of 0.2% seen in the simulation. Thus, molecular diffusion plays a significant role in reducing the polarization in a long channel. As a matter of fact, it is possible to determine the approximate $(P_I^{(b)})_{lim} \ll 1$) steady-state solution $P_I^{(b)}(y)$ for Eq. (6) if $v=0$. One finds:

$$P_I^{(b)}(y) = \begin{cases} (P_I^{(b)})_{lim}\left(1 - \exp\left(-\frac{y_I/2}{\sqrt{DT_{1I}^{(b)}}}\right)\right) \cosh\left(\frac{y}{\sqrt{DT_{1I}^{(b)}}}\right) & \text{if } |y| \leq \frac{y_I}{2} \\ (P_I^{(b)})_{lim} \sinh\left(\frac{y_I/2}{\sqrt{DT_{1I}^{(b)}}}\right) \exp\left(\frac{|y|}{\sqrt{DT_{1I}^{(b)}}}\right) & \text{if } |y| \leq \frac{y_I}{2} \end{cases} \quad (6)$$

Thus, the limit polarization in an infinite channel is $(P_I^{(b)})_{lim}(1-\exp(-y_I/\sqrt{4DT_{1I}^{(b)}})) \approx -0.2\%$ in agreement with the simulation.

Since $f \ll 1$, the formula for bulk nuclear spin polarization when the NVs are pumped into $m_S=0$ takes the approximate form $$(P_I^{(b)})_{max} \approx -fT_{1I}^{(b)}(W_2-W_0), \quad (7)$$

where $T_{1I}^{(b)}$ is the nuclear spin-lattice relaxation time of molecules removed from the walls. For example, for a typical protonated solvent—where $T_{1I}^{(b)}$ is of the order of 5-10 s—one obtains $(P_I^{(b)})_{lim} \approx 10^{-2}$ for realistic surface conditions (Supplementary Section S4). This latter value must be understood, however, as an upper bound since molecular diffusion away from the illuminated area during the buildup time (of order $T_{1I}^{(b)}$) necessarily reduces the final nuclear spin polarization. This is illustrated in FIG. 7A, where the numerical integration of an adapted convection-diffusion equation yields a peak proton polarization in water of 0.2%. This polarization is remarkably high considering that the thermal proton spin polarization in the assumed ~100 mT field amounts to just 5×10$^{-7}$. Greater polarization levels may be possible in select gases where $T_{1I}^{(b)}$ can be considerably longer than in a liquid, provided the target system can be properly confined during the pumping process.

In a practical application, a tradeoff exists between the bulk polarization of the outgoing fluid and the flow rate. The critical parameter is the transit time $\tau_t$ across the NV-implanted region. The stationary nuclear spin polarization of proton spins in bulk water was calculated during transit and after exiting the diamond microstructure for two different flow rates. We find a level of polarization similar to that obtained in FIG. 7A when $\tau_t \approx T_{1I}^{(b)}$, though in the regime of continuous flow the polarized fluid can only be transported over a distance comparable to the size of the implanted region (of length $y_I$ in the sketch of FIG. 7A). The opposite applies for greater flow rates, namely, the delivery range increases at the expense of the final bulk polarization. Transport of optimally polarized fluids over longer distances could be attained by illuminating a larger area (see below), by operating in batch mode, or by making the transport channel narrower than the polarization channel. The fluid polarization is approximately uniform throughout the channel width $z_w$ (see polarization map in FIG. 7A). The latter reflects the fact that the diffusion time $\tau_w \sim z_w^2/D$ in a fluid of self-diffusion coefficient D (~100 microseconds for molecules in water, the model fluid in this example) is typically much smaller than the nuclear polarization time ~$(W_2 + W_0)^{-1}$ (of order ~1 s for the assumed magnetic field and surface conditions).

From Eq. (7) we conclude that the limit polarization in the fluid is largely dominated by the chosen working geometry via the fraction of time f≪1 molecules spend in contact with the diamond surface. While further reducing the inter-wall separation in the channel is an obvious way to increase f, an alternate route is to enhance the overall surface via the use of 3D structures. For example, plasma etching techniques already introduced for the scalable fabrication of nanowires and nanocrystals from single diamond crystals could be adapted to produce a set of vertical pillars randomly distributed throughout an otherwise flat microfluidic channel. Along the same lines, one can envision systems where the fluid permeates through diamond nanocrystals arrayed in a packed-bed-type geometry. Further work will be required, however, to account for the probabilistic alignment between the NV axis and the applied magnetic field.

The volume of maximally polarized fluid that can be generated per unit time largely depends on the size of the optically pumped area, which, for the vertical illumination assumed in FIG. 7A, would be restricted to less than ~(30-50 micrometer)$^2$ for reasonable laser intensities (~1 mW/μm$^2$ are typically required to pump NV centers on the microsecond time scale). Geometries where light is injected laterally into thin diamond sheets of larger surface area are, however, a conceivable way to circumvent this limitation, especially if the sheets are embedded within cavity-like structures designed to reflect and redistribute light efficiently throughout the entire surface.

NV-DNP could circumvent several complications found in other hyperpolarization schemes. For example, unlike in para-hydrogen-based methods, no chemical reaction is required, which also makes the polarization transfer insensitive to the chemical structure of the target molecule (thus eliminating the typical antiphase doublets in the resulting NMR spectra). NV-DNP shares the same hyperpolarization principles governing the use of dissolved radicals or semiconductor nanoparticles, but the NV optical pumping and the zero field spin splitting inherent to this defect make this approach of special interest. Dynamic nuclear polarization of atomic and molecular gases is a particularly interesting application as the fraction of molecules adsorbed on the diamond surface—and thus the concomitant nuclear spin polarization, see Eq. 5—could be greatly enhanced by moderately reducing the gas temperature.

NV-DNP can be extended in several ways including the use of Hartman-Hahn protocols to polarize near-surface paramagnetic impurities or $^{13}$C spins, which can then cross-relax with the nuclear spin of the fluid. For example, delta doping, diamond overgrowth, and surface termination could be combined to create ultra-pure $^{13}$C-enriched films capable of transferring polarization to the outside fluid without the need for a direct coupling with the NV layer; further work, however, is needed to assess the efficiency of these or similar schemes. By the same token, paramagnetic defects other than the NV center could also serve as polarization sources; examples are the di-vacancy and silicon-vacancy centers in SiC, and rare-earth ions in YAG.

It is worth highlighting the relative simplicity of the hardware required in a practical implementation: Unlike the most advanced forms of DNP—integrating sophisticated microwave instrumentation, a freeze-thaw cycle, and a sample-shuttling protocol—an NV-DNP system would take the form of a compact optofluidic chip within a bench-top magnet. This versatility could pave the way to numerous applications including laboratory and point-of-care diagnostics, combinatorial synthesis and screening, food safety, environmental testing, scientific studies of mass-limited systems, and the detection of hazardous biochemical agents.

Rather than polarizing nuclear or electronic spins in molecules adsorbed to the diamond surface one can also polarize mobile charge carriers (electrons or holes) circulating near the paramagnetic centers.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for polarizing nuclear or electronic spins, the method comprising steps of:
    introducing an analyte into a channel, wherein at least one surface of the channel is a substrate comprising a plurality of spin defect centers implanted inside 10 nm of the at least one surface of the channel;
    exposing the spin defect centers to a magnetic field of at least 500 gauss while the analyte is in the channel;
    illuminating the plurality of spin defect centers with light to produce polarized spins in the spin defect centers, the step of illuminating occurring while the analyte contacts the at least one surface, thereby positioning the analyte proximate the polarized spins; and
    permitting the polarized spins in the spin defect centers to induce spin polarization in the analyte.

2. The method as recited in claim 1, the method further comprising detecting the analyte based on its induced spin polarization.

3. The method as recited in claim 2, wherein the step of detecting the analyte is performed by irradiating the induced spin polarization in the analyte with an electromagnetic wave and observing a signal produced by the analyte in response to the electromagnetic wave.

4. The method as recited in claim 1, wherein the spin defect centers are present in a concentration between about $10^{11}$ and $10^{13}$ spin defect centers per square centimeter inside 10 nm of the at least one surface.

5. The method as recited in claim 1, wherein the step of permitting the polarized spins in the spin defect centers to induce spin polarization in the analyte causes at least 0.001% of the analyte's spins to be polarized.

6. The method as recited in claim 1, wherein the step of permitting the polarized spins in the spin defect centers to induce spin polarization in the analyte causes at least 0.003% of the analyte's spins to be polarized.

7. The method as recited in claim 1, wherein the step of permitting the polarized spins in the spin defect centers to induce spin polarization in the analyte causes at least 0.001% of the analyte's spins to be polarized while the magnetic field is 1 T or less.

8. The method as recited in claim 1, wherein the substrate is a semiconductor.

9. The method as recited in claim 1, wherein the substrate is a wide bandgap material.

10. The method as recited in claim 1, wherein the substrate is a silicon carbide substrate and the spin defect centers are selected from the group consisting of Photo-Luminescence 5 (PL5) defects and Photo-Luminescence 6 defects (PL6).

11. The method as recited in claim 1, wherein the substrate is a diamond crystal substrate and the spin defect centers are nitrogen-vacancy centers.

12. The method as recited in claim 11, wherein the channel is a microfluidic channel having a width of at least about 50 nm and less than about 50 microns.

13. The method as recited in claim 12, wherein the microfluidic channel has a depth of at least 80 nm and less than 50 microns.

14. The method as recited in claim 12, wherein the microfluidic channel has a depth of at least 100 nm and less than 10 microns.

15. The method as recited in claim 11, wherein the channel is disposed within a polymeric layer disposed next to the substrate such that at least three surfaces of the channel are formed from the polymeric layer and a fourth surface of the channel is the at least one Surface of the channel.

16. The method as recited in claim 11, wherein the channel is within the substrate such that at least three surfaces of the channel are formed from the substrate one of which is the at least one surface of the channel.

17. The method as recited in claim 16, wherein the at least three surfaces each comprise spin defect centers inside 10 nm of their respective surface.

18. The method as recited in claim 11, wherein the at least one surface has a surface-roughness with trenches having a depth of between about 5 nm and about 10 microns.

* * * * *